(12) United States Patent
Sartor

(10) Patent No.: US 7,871,392 B2
(45) Date of Patent: Jan. 18, 2011

(54) ENDOSCOPIC ULTRASONIC SURGICAL ASPIRATOR FOR USE IN FLUID FILLED CAVITIES

(75) Inventor: Joe D. Sartor, Longmont, CO (US)

(73) Assignee: Integra LifeSciences (Ireland) Ltd., Dublin (IR)

( * ) Notice: Subject to any disclaimer, the term of this patent is extended or adjusted under 35 U.S.C. 154(b) by 1188 days.

(21) Appl. No.: 11/330,626

(22) Filed: Jan. 12, 2006

(65) Prior Publication Data

US 2007/0162050 A1 Jul. 12, 2007

(51) Int. Cl.
*A61B 17/20* (2006.01)
(52) U.S. Cl. .............................. 604/22; 604/27; 604/35
(58) Field of Classification Search ............. 604/19–22, 604/27, 35, 43
See application file for complete search history.

(56) References Cited

U.S. PATENT DOCUMENTS 5,151,083 A * 9/1992 Pichler ........................ 604/22
5,163,433 A * 11/1992 Kagawa et al. ................. 601/2
5,334,183 A * 8/1994 Wuchinich .................... 606/46
5,484,398 A * 1/1996 Stoddard ...................... 604/22
6,013,048 A * 1/2000 Podany et al. ................. 604/22

* cited by examiner

*Primary Examiner*—Kevin C Sirmons
*Assistant Examiner*—Bhisma Mehta
(74) *Attorney, Agent, or Firm*—Thomas A. Runk; Fulwider Patton LLP

(57) ABSTRACT

An ultrasonic horn assembly is configured so that irrigating fluid can be supplied only to a vibrating tip portion of the ultrasonic horn and so that suction aspiration can occur through a portion of the ultrasonic horn not in contact with the irrigating fluid. Controllers supplying irrigation fluid during a surgical procedure and controlling suction aspiration via monitoring of fluid level in the patient cavity are operatively coupled one to another to coordinate control of the fluid level in the patient cavity. Circuitry controlling power, frequency and amplitude of the tip of the ultrasonic horn occurring as a result of operation of a source of ultrasonic signal generating power controls either or both the supply of irrigation fluid and the suction aspiration so as to minimize damping of vibration of the tip of the ultrasonic horn. An optical viewing element is provided to view the tip of the ultrasonic horn.

26 Claims, 2 Drawing Sheets

ENDOSCOPIC ULTRASONIC SURGICAL ASPIRATOR FOR USE IN FLUID FILLED CAVITIES

BACKGROUND

1. Technical Field

This disclosure relates to surgical systems and, more particularly, to ultrasonic horns for fragmenting tissue in fluid filled cavities during a surgical procedure.

2. Background of Related Art

It is known in the art of applying ultrasonic horns for fragmenting tissue in fluid filled cavities during a surgical procedure that energy is absorbed or dispersed from ultrasonic tips by fluid along the tip length. If fluid fills a flue around an ultrasonic tip or is aspirated without air inside of the tip, the energy loss renders the tip inoperative. Such conditions are most severe when an ultrasonic tip is used in environments such as a ventricle of the brain.

What is needed is a method of irrigating tissue which isolates an ultrasonic tip from irrigation fluid, and provides an air path so that the condition rendering the tip as inoperative is mitigated or completely eliminated, even in environments such as a ventricle of the brain.

SUMMARY

It is an object of the present disclosure to provide an ultrasonic horn and assembly which is configured to supply irrigating fluid only to a vibrating tip portion and to aspirate through a portion of the ultrasonic horn not in contact with the irrigating fluid.

It is an object of the present disclosure to provide an ultrasonic horn assembly system in which controllers supply irrigation fluid during a surgical procedure and control suction aspiration via monitoring of fluid level in the patient cavity are operatively coupled to coordinate control of the fluid level in the patient cavity.

It is an object of the present disclosure to provide an ultrasonic horn having circuitry which controls power, frequency and amplitude of the tip of the ultrasonic horn occurring as a result of operation of a source of ultrasonic signal generating power controls either or both the supply of irrigation fluid and the suction aspiration so as to minimize damping of vibration of the tip of the ultrasonic horn.

According to an aspect of the present disclosure, an ultrasonic horn assembly is provided and includes a flue; an ultrasonic horn operatively disposed within the flue, the ultrasonic horn assembly being configured to supply irrigating fluid only to a vibrating tip portion of the ultrasonic horn and to aspirate through a portion of the ultrasonic horn located proximally of the vibrating tip portion; and an optical viewing element operatively connected to the flue and configured to view at least the vibrating tip portion of the ultrasonic horn.

The ultrasonic horn assembly may further include an adapter having a proximal end and a distal end, the proximal end of the adapter being configured to connect to an ultrasonic resonator; an elongated member having an outer surface, a proximal end and a distal end, the distal end of the adapter being joined to the proximal end of the elongated member, and an internal channel formed within the adapter and the elongated member, the internal channel extending from the proximal end of the elongated member to the distal end of the elongated member, the internal channel having a first aperture at a distal end thereof, the distal end of the elongated member being the vibrating tip of the ultrasonic horn, the elongated member having a first aperture formed in the outer surface thereof and being in fluidic communication with the internal channel.

The ultrasonic horn assembly may further include a housing having an inside surface and an outside surface, the inside surface of the housing at least partially encasing the elongated member, wherein a first internal space is defined between the housing and the elongated member. The flue may at least partially encase the housing. The flue may have an inside surface and an outside surface, wherein the inside surface of the flue at least partially encases the distal end of the elongated member. The ultrasonic horn assembly may further include a second internal space defined between the flue and the housing and between the flue and the distal end of the elongated member. The first internal space may be in fluidic communication with the second internal space via a passage formed in the housing, and the first internal space may also be in fluidic communication with the internal channel formed within the elongated member via the second aperture formed in the elongated member.

The ultrasonic horn assembly may further include a seal for inhibiting fluidic communication between the first internal space and the second internal space.

It is envisioned that the proximal end of the adapter includes a connecting portion for coupling with at least one of the ultrasonic horn and an ultrasonic resonator. It is further envisioned that the housing encloses the elongated member, the adapter, and the ultrasonic resonator.

The ultrasonic horn assembly may further include a supply of irrigation fluid fluidically coupled to the ultrasonic horn so as to supply irrigation fluid only to the vibrating tip portion of the ultrasonic horn; and a source of suction aspiration fluidically coupled to the internal channel of the ultrasonic horn, only at a location proximal of the vibrating tip portion.

The ultrasonic horn assembly may still further include a supply of irrigation fluid fluidically coupled to the ultrasonic horn so as to supply irrigation fluid only to the vibrating tip portion of the ultrasonic horn; and a source of suction aspiration fluidically coupled to the internal channel of the ultrasonic horn, only at a location proximal of the vibrating tip portion. The supply of irrigation fluid may be fluidically coupled to the second internal space formed between the flue and the housing, and to a space between the flue and the distal end portion of the elongated member; and the source of suction aspiration may be fluidically coupled to the internal channel formed within the adapter and the elongated member of the ultrasonic horn.

The ultrasonic horn assembly may further include a controller that controls the supply of irrigation fluid via monitoring of fluid level in a patient cavity during a surgical procedure; and a controller that controls the suction aspiration applied by the source of suction aspiration via monitoring of fluid level in the patient cavity during the surgical procedure.

In an embodiment, the controller that controls the supply of irrigation fluid via monitoring of fluid level in a patient cavity during a surgical procedure and the controller that controls the suction aspiration applied by the source of suction aspiration via monitoring of fluid level in the patient cavity during the surgical procedure are operatively coupled one to another to coordinate control of the fluid level in the patient cavity.

The ultrasonic horn assembly may further include a source of ultrasonic signal generating power operatively coupled to the ultrasonic handpiece; and circuitry controlling at least one of power, frequency and amplitude of the tip of the ultrasonic horn occurring as a result of operation of the source of ultrasonic signal generating power.

The ultrasonic horn assembly may still further include a source of ultrasonic signal generating power operatively coupled to the ultrasonic handpiece; and circuitry controlling at least one of power, frequency and amplitude of the tip of the ultrasonic horn occurring as a result of operation of the source of ultrasonic signal generating power.

It is envisioned that the circuitry controlling at least one of power, frequency and amplitude of the tip of the ultrasonic horn occurring as a result of operation of the source of ultrasonic signal generating power controls at least one of the supply of irrigation fluid and the suction aspiration so as to minimize damping of vibration of the tip of the ultrasonic horn.

In an embodiment, the optical viewing element may be disposed to enable viewing the vibrating tip of the ultrasonic horn. The optical viewing element may be disposed within a channel member formed in the flue and extends to a distal end portion of the flue such that the optical viewing element is capable of viewing, through a viewing angle, the tip of the ultrasonic horn.

The ultrasonic horn assembly may further include a controller for varying a position of the optical viewing element.

According to another aspect of the present disclosure, a method of ultrasonic surgical aspiration, performed by an ultrasonic horn assembly, is provided. The method includes the steps of supplying irrigation fluid to the ultrasonic horn assembly, the irrigation fluid being in contact with an ultrasonic horn of the ultrasonic horn assembly only at a vibrating tip portion of the ultrasonic horn; and aspirating an internal channel in the ultrasonic horn which transmits ultrasonic energy to patient tissue, wherein the aspirating occurs at a portion of the ultrasonic horn that is located proximally of the vibrating tip portion.

The method may further include the steps of controlling the supply of irrigation fluid via monitoring of fluid level in a patient cavity during a surgical procedure; and controlling the suction aspiration via monitoring of fluid level in the patient cavity during the surgical procedure.

The method may further include the steps of controlling at least one of power, frequency and amplitude of the tip of the ultrasonic horn occurring as a result of operation of a source of ultrasonic signal generating power to the ultrasonic horn.

It is envisioned that the steps of controlling the supply of irrigation fluid via monitoring of fluid level in a patient cavity during a surgical procedure and controlling the suction aspiration via monitoring of fluid level in the patient cavity during the surgical procedure may be performed by coordinating with the controlling of at least one of power, frequency and amplitude of the tip of the ultrasonic horn occurring as a result of operation of a source of ultrasonic signal generating power to the ultrasonic horn so as to minimize damping of vibration of the tip of the ultrasonic horn.

The method may further include the step of viewing the vibrating-tip of the ultrasonic horn. The method may further include the step of varying a position of an optical viewing element disposed for viewing the vibrating tip of the ultrasonic horn.

BRIEF DESCRIPTION OF THE DRAWINGS

Embodiments of the presently disclosed ultrasonic horn are described herein with reference to the drawings, wherein.

DETAILED DESCRIPTION

Figure 1:
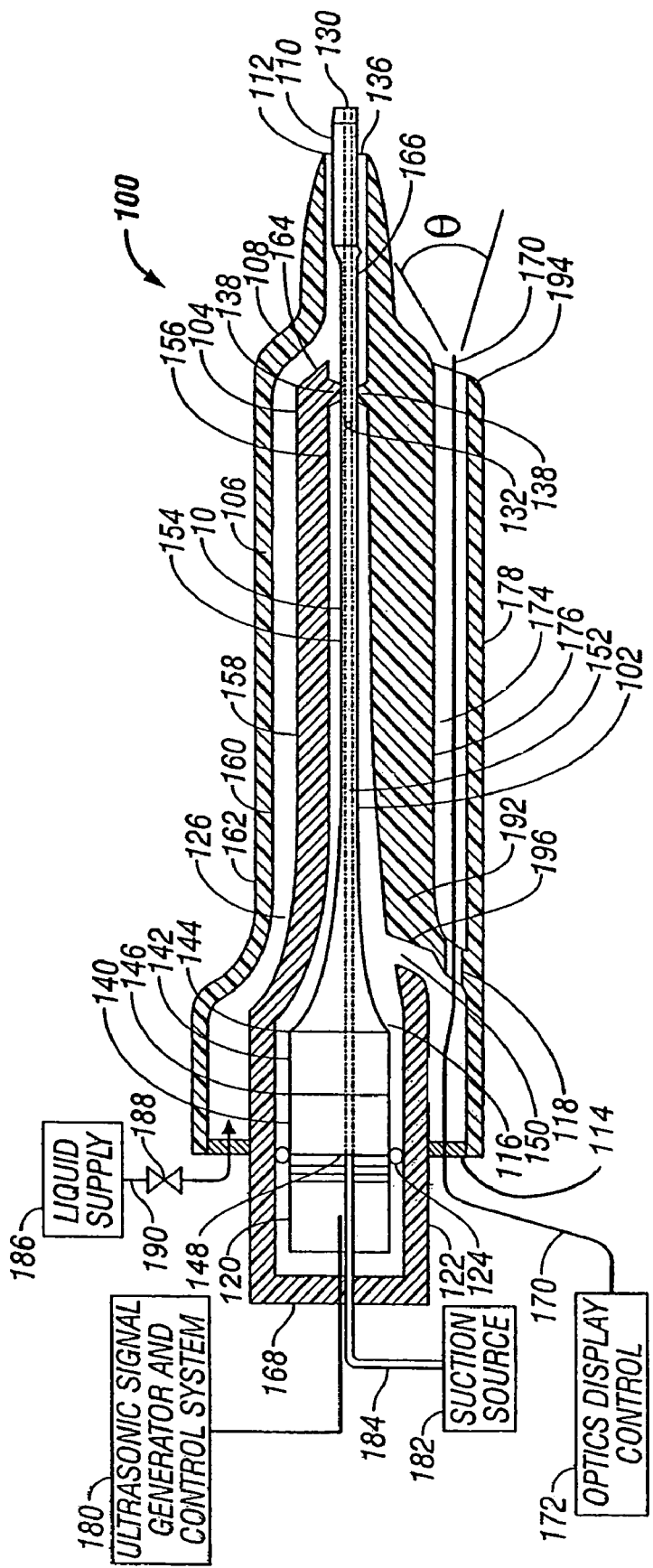
FIG. 1 is a cross-sectional view of one embodiment of an ultrasonic horn assembly of the present disclosure illustrating that irrigating fluid can be supplied only to a vibrating tip portion of an ultrasonic horn and suction aspiration can occur through a portion of the ultrasonic horn not in contact with the irrigating fluid.

Embodiments of the presently disclosed ultrasonic horn will now be described in detail with reference to the drawings, in which like reference numerals designate identical or corresponding elements in each of the several views. As used herein, the term "distal" refers to that portion of the instrument, or component thereof which is further from the user while the term "proximal" refers to that portion of the instrument or component thereof which is closer to the user.

FIG. 1 illustrates one embodiment of the present disclosure of an ultrasonic horn assembly 100 which is adapted for use in an ultrasonic surgical system having an ultrasonic resonator and irrigation and aspiration channels. An example of such an ultrasonic surgical system is disclosed in commonly owned WIPO International Publication Number WO 2004/026150 A2 by Garrison et al. and assigned to Sherwood Services AG, a division of Tyco Healthcare Group LP, the entire contents of which are incorporated herein by reference.

More particularly, FIG. 1 illustrates an ultrasonic horn assembly 100 for an ultrasonic surgical device. As is described in more detail below, the ultrasonic horn assembly 100 includes an ultrasonic horn 10, a flue 106 which protects surrounding tissue from inadvertent contact with the horn 10, and which provides a means of flowing irrigation to the tip of the horn 10. Specifically, ultrasonic horn 10 includes an elongated member 102 having a proximal end 144 and a distal end 110. The distal end 110 of the elongated member 102 is the vibrating tip portion 110 of the horn. Elongated member 102 includes an adapter 142 having a proximal end 146 and a distal end which is coincident with the proximal end 144 of elongated member 102, i.e., the distal end of the adapter 142 is joined to, or coincident with, the proximal end 144 of elongated member 102. Proximal end 146 of adapter 142 is configured to connect to a connecting portion 140. Connecting portion 140 is configured to couple ultrasonic horn 10 to an ultrasonic resonator transducer 120.

Elongated member 102 further includes an outside surface 154. An internal channel 152 is formed within adapter 142 and elongated member 102. Channel 152 extends from proximal end 144 to distal end 110 of elongated member 102. Channel 152 has a first aperture 130 at distal end 110 and a second aperture 132 on outside surface 154 of elongated member 102 which is in fluidic communication with channel 152.

Ultrasonic horn assembly 100 further includes a housing 104 which has an inside surface 156 and an outside surface 158. Inside surface 156 of housing 104 at least partially encases elongated member 102C2 "and is larger than the diameter of the elongated member 102" to form a first internal space 116 therebetween. Housing 104 is formed from a substantially rigid material such as, polycarbonate.

A flue 106 at least partially encases housing 104. Flue 106 is formed from a substantially flexible material such as silicone or the like and includes an outside surface 162. Also, an inside surface 160 of flue 106 at least partially encases a portion 166 of elongated member 102 at distal end 110 and is larger than the diameter of the elongated member 102, so that a lumen or second internal space 126 is thereby formed between flue 106 and housing 104 and between flue 106 and the portion 166 of elongated member 102 at distal end 110.

The second internal space 126 is separate from the first internal space 116 and the second internal space 126 is open at the distal end 112 of the flue 106. The flue 106 is adapted such that irrigation fluid applied to the second internal space 126 flows out the distal end of the flue 106 over the vibrating tip portion 110.

The flue 106 and the housing 104 also partially join to form a common section 192 on a lower portion of the ultrasonic horn assembly 100. As a result, the first internal space 116 formed between the inside surface 156 of housing 104 and elongated member 102 is in fluidic communication with the second internal space 126 formed between flue 106 and housing 104 and between flue 106 and the portion 166 of elongated member 102 at distal end 110 via a passage 150 formed in the housing 104. The passage 150 may be located in proximity to a proximal end 196 of the common section 192. In addition, first internal space 116 is in fluidic communication with internal channel 152 formed within elongated member 102 via second aperture 132 in elongated member 102. Consequently, first internal space 116 is in fluidic communication with first aperture 130 at distal end 110 of elongated member 102.

Housing 104 extends to form an enclosure housing 122 at a proximal end 168. Typically, ultrasonic horn 10 includes adapter 142 and elongated member 102. As illustrated in FIG. 1, ultrasonic horn 10 is connected to connecting body 140 and to ultrasonic resonator transducer 120. An ultrasonic signal generator and control system 180 is connected to ultrasonic resonator transducer 120 through housing 104. O-ring supports 124 are disposed between connecting body 140 and inner surface 156 of the housing 104. In one embodiment, the O-ring supports 124 are disposed at a proximal end or joint 148 between connecting body 140 and resonator transducer 120. The O-ring supports 124 therefore support ultrasonic horn 10 within housing 104.

Flue 106 has a proximal end 114 and a distal end 112. An aperture 136 is formed at distal end 112 of flue 106. Distal end 110 of elongated member 102 extends beyond aperture 136 so that a patient tissue can be treated effectively by ultrasonic energy emitted by ultrasonic horn assembly 100. Proximal end 114 of flue 106 seals the second internal space 126 between inside surface 160 of the flue 106 and outside surface 158 of the housing 104. Those skilled in the art will recognize that there are alternative configurations for the proximal end 114 such as being open rather than sealed. Proximal end 114 is illustrated as sealed herein by way of example only.

A liquid irrigation supply 186 fluidically communicates, via a supply line 190 which penetrates proximal end 114, with the second internal space 126 formed between flue 106 and housing 104 and between flue 106 and the portion 166 of elongated member 102 at distal end 110. The irrigation supply fluid 186 is a fluid such as a saline solution or other fluid appropriate for the protocol being performed. Flow from fluid supply 186 is controlled via a valve 188 disposed in supply line 190. Therefore, liquid irrigation fluid is in fluidic communication with the aperture 136 at distal end 112 of flue 106. To further enhance cooling and isolation of the fluid, a seal 138 is disposed at a distal end 164 of the housing 104, and distal of the second aperture 132, to at least inhibit or completely seal fluidic communication between first internal space 116 space 126 and second internal space 126. The vibrating tip portion 110 protrudes distally beyond the distal end 164 of the housing 104 and protudes distally beyond the distal end 112 of the flue 106. The seal 138 is disposed between the housing 104 and the elongated member 102 at a position proximal to the vibrating tip portion 110. The seal 138 is configured to inhibit fluids entering into the first internal space 116 from the distal end 112 of the flue 106 and to inhibit fluids exiting the first internal space 116 at the distal end 164 of the housing 104 to reach the vibrating tip portion 110.

A suction source 182 fluidically communicates with internal channel 152 within elongated member 102 via a non-collapsible suction line 184 which penetrates the proximal end 168 of the enclosure housing 122.

It may be required for a user to view the tip 110 of the horn 10 during the surgical procedure. It is envisioned that the flue can be configured as part of an endoscope or can be configured with an optical viewing element 170 which may be either partially included in the flue 106 and/or transported through a channel 174 formed in flue 106. The channel 174 may be formed in a lower surface 176 of the common portion 192, or the channel 174 may be formed via a peripheral wall 178 at least partially extending around the lower surface 176. The channel 174 extends distally to a tapered portion 108 of the flue 106, near the distal end 112 thereof. The peripheral wall 178 extends to a distal end 194 in the vicinity of the tapered portion 108.

The optical viewing element 170 can be an optical fiber bundle or a microlens which penetrates the proximal end 114 of flue 106 and is disposed through the second internal space 126 and through a passage 118 through common portion 192 communicating through to channel member 174.

In one embodiment, optical viewing element 170 extends to the distal end 194 of the channel 174 in the vicinity of the tapered portion 108 such that the optical viewing element 170 is capable of viewing the tip portion 110 of the horn 10 during the surgical procedure through a viewing angle "θ". The viewing angle "θ" ranges from about 0° to about 180°.

Optical fiber bundles and micro lenses are now commercially available in the range of 0.5 to 1.0 mm in diameter. In one embodiment, the optical viewing element or optic fiber bundle 170 is inserted inside of the flue 106 as opposed to the optics being placed down a separate endoscope. The optical fiber bundle 170 is connected to an optics display 228 and control 172 which can be external to the ultrasonic horn assembly 100.

During operation of the ultrasonic horn in a deep cavity, the utilization of a long or multi-wavelength tip is sufficient to isolate the irrigation fluid. In surgical applications in which tip portion 110 is immersed in fluid, e.g., applications involving ventricles of the brain, ultrasonic horn assembly 100 effects isolation of the irrigation fluid to minimize energy losses and allow for operation of the assembly 100. Where immersion of tip portion 110 is necessary, the use of a fluid regulation system that ensures that the irrigation rate matches or exceeds the aspiration rate so as to avoid draining the ventricle is recommended. This fluid control system could function through a closed loop monitoring flow or volume/weight of fluid aspirated versus fluid irrigated or it can simply be set to a flow rate higher than the aspiration rate and allow the excess to drain away as is typical of arthroscopic procedures.

Figure 2:
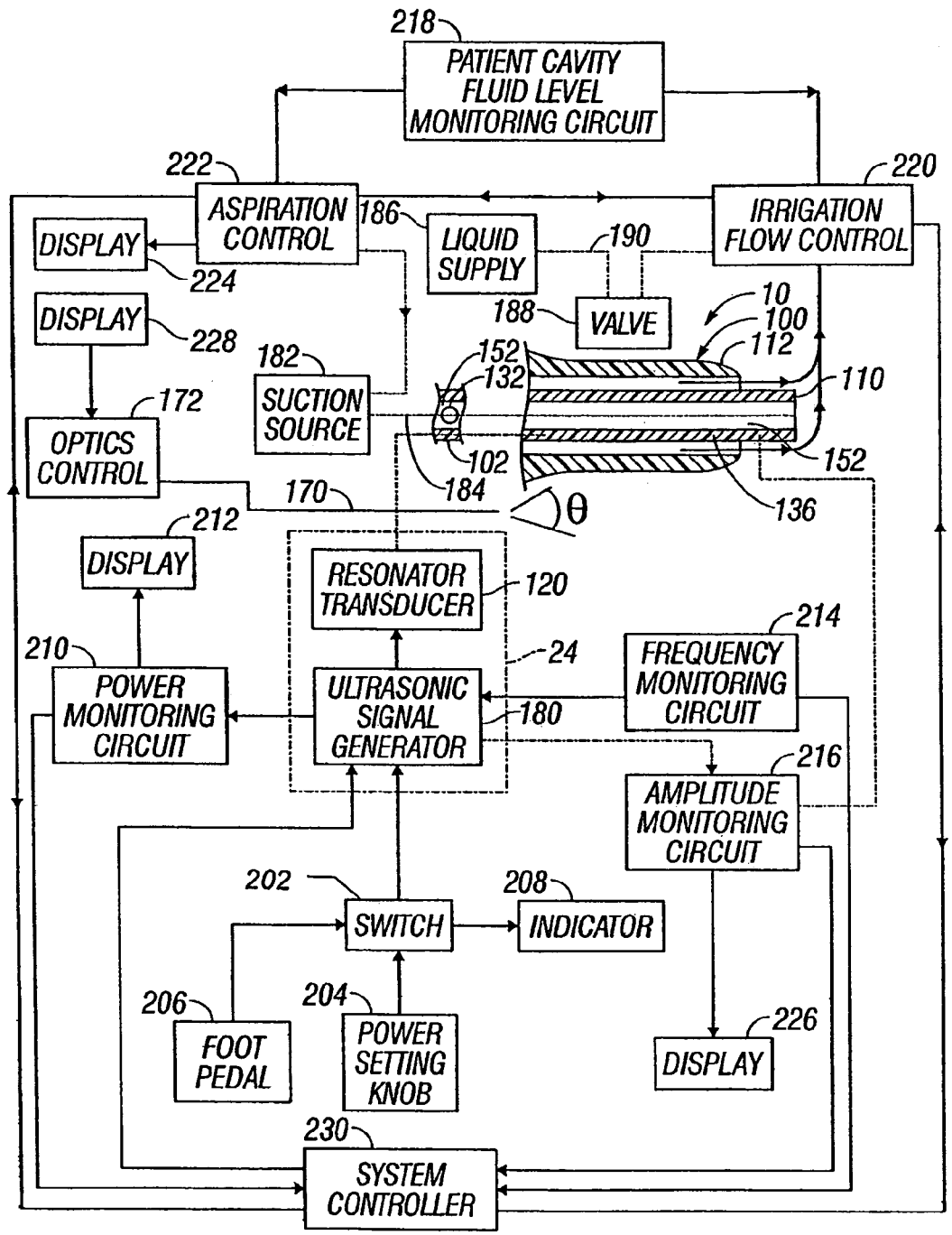
FIG. 2 is a schematic diagram of the instrumentation and control systems for the ultrasonic horn assembly of FIG. 1.

FIG. 2 is a schematic diagram of the operation and control systems of ultrasonic horn assembly 100. More particularly, FIG. 2 illustrates the portion 166 of elongated member 102 at distal end 110. Optical viewing element or optical fiber bundle 170 extends to tapered end 108 at distal end 110 via channel 174. Distal end 110 is the vibrating resonant tip of ultrasonic horn 10. As best shown in and previously discussed with respect to FIG. 1, liquid irrigation supply fluid 186 fluidically communicates, via a supply line 190 to second internal space 126 formed in part between flue 106 and portion 166 of elongated member 102 at distal end 110. Flow from fluid supply 186 is controlled via valve 188 disposed in supply line 190. Liquid irrigation supply fluid 186 fluidically communicates with aperture 136 at distal end 112 of flue 106 which is immediately proximal to vibrating tip portion 110.

As noted previously, suction source 182 fluidically communicates with the internal channel 152 within elongated member 102 via non-collapsible suction line 184 in flue 106 and second aperture 132 on outside surface 154 of elongated member 102.

Therefore, the supply of irrigation fluid 186 is fluidically coupled to ultrasonic horn 10 so as to supply irrigation fluid 186 only at vibrating tip portion 110 of ultrasonic horn 10, and the source of suction aspiration 182 is fluidically coupled to internal channel 152 in ultrasonic horn 10 only at a portion of ultrasonic horn 10 not in contact with irrigation fluid 186.

In addition, the source of ultrasonic power 24 comprises a signal generating power supply 180 operatively coupled to the ultrasonic handpiece or resonator transducer 120. Ultrasonic signal generating power supply 180 is initiated via power switch 202. The power level is set and/or adjusted typically by means known in the art such as power setting knob 204 or footpedal 206. An indicating light 208 indicates whether the power setting knob 204 or footpedal 206 is connected. Power output by the ultrasonic signal generator 180 is measured by power output meter 210 and displayed by power display 212. The frequency of the vibrating tip portion 110 is measured by frequency monitoring circuit 214. Correspondingly, the amplitude of the vibrating tip portion 110 is measured by amplitude monitoring circuit 216. The frequency and amplitude measurements can be displayed either independently such as on display 226 or on a common display such as display 212.

During operation of the ultrasonic horn assembly, the source of ultrasonic signal generating power 180 is operatively coupled to ultrasonic handpiece or resonator transducer 120. System controller 230, which can be circuitry such as a microprocessor or substantially equivalent device, receives the measurements of power, frequency and amplitude of vibrating tip portion 110 from power output meter 210, frequency monitoring circuit 214, and amplitude monitoring circuit 216. System controller circuitry 230 controls at least one of power, frequency and amplitude of the tip portion 110 of ultrasonic horn 10 occurring as a result of operation of the source of ultrasonic signal generating power 180.

In addition, during operation of the ultrasonic horn assembly, the flow of irrigation fluid to a cavity in the patient is monitored by patient cavity fluid level monitoring circuit 218 through the irrigation flow control 220. Measurement of the patient cavity fluid level is communicated to an irrigation flow valve 188 through the irrigation flow control 220 which controls the supply of irrigation fluid 186 via monitoring of fluid level in the patient cavity during a surgical procedure.

Correspondingly, measurement of patient cavity fluid level is also communicated to an aspiration controller 222 that controls the suction aspiration applied by the source of suction aspiration 182 also via monitoring of fluid level in the patient cavity during the surgical procedure.

In a variation of the embodiment of the present disclosure, controller 220 that controls the supply of irrigation fluid 186 via monitoring of fluid level 220 in a patient cavity during a surgical procedure and controller 222 that controls the suction aspiration applied by the source of suction aspiration 182 also via monitoring of fluid level 220 in the patient cavity during the surgical procedure may be operatively coupled one to another to coordinate control of the fluid level in the patient cavity.

In addition, the circuitry controlling at least one of power, frequency and amplitude, e.g., system controller 230, of tip portion 110 of ultrasonic horn 10 occurring as a result of operation of the source of ultrasonic signal generating power supply 180 can also be configured to control at least one of the supply of irrigation fluid 186 and the suction aspiration 182 so as to minimize damping of vibration of tip portion 110 of ultrasonic horn 10. The irrigation flow control parameters and the aspiration control parameters can be displayed either independently or on a common display such as display 224.

To further facilitate the surgical procedure by the user, optical viewing element 170 which is disposed in proximity to the vibrating tip to enable viewing the vibrating tip of ultrasonic horn 10 can be controlled by optics controller 172 and the optical results displayed on display 228. Optics controller 172 can vary the position of the optical viewing element 170.

Consequently, in view of the foregoing ultrasonic horn assembly 100 and system of the present disclosure as disclosed by FIGS. 1 and 2, the user can implement a method of ultrasonic surgical aspiration by the ultrasonic horn assembly comprising the steps of supplying irrigation fluid 186 to ultrasonic horn assembly 100, with the irrigation fluid 186 in contact with ultrasonic horn 10 of the ultrasonic horn assembly 100 only at the vibrating tip portion 110 of ultrasonic horn 10 and aspirating internal channel 152 in ultrasonic horn 10 which transmits ultrasonic energy to patient tissue, with the aspirating occurring at a portion of ultrasonic horn 10 that is not in contact with the irrigating fluid 186, e.g., at second aperture 132 on outside surface 154 of elongated member 102.

Furthermore, the method is implemented in one embodiment by monitoring of fluid level 218 in the patient cavity during the surgical procedure and controlling the supply of irrigation fluid 186 via irrigation flow controller 220 and controlling via aspiration controller 222 the suction aspiration by the suction source 182. The method also can include controlling at least one of the power, frequency and amplitude, via power monitoring circuit 210, and/or frequency monitoring circuit 214, and/or amplitude monitoring circuit 216, of vibrating tip portion 110 of ultrasonic horn 10 occurring as a result of operation of the source of ultrasonic signal generating power 180 to the ultrasonic horn 10.

In one embodiment of the present disclosure, the method can include the step of coordinating controlling the source of ultrasonic signal generating power 180 to the ultrasonic horn 10 so as to minimize damping of vibration of the tip portion 110 of the ultrasonic horn 10.

In one embodiment of the present disclosure, to facilitate the surgical procedure by the user, the method can also include the step of viewing vibrating tip portion 110 of ultrasonic horn 10, e.g., via the optical viewing element 170. Also, the field of view afforded to the user can be changed by varying the position of the optical viewing element 170 using optics controller 172, which is disposed for viewing vibrating tip portion 110 of ultrasonic horn 10.

It can be seen then that the fluid control system and method, based on the patient cavity monitoring circuit 218, ensures that the irrigation rate matches or exceeds the aspiration rate so as to avoid draining a patient cavity such as a ventricle of the brain. This fluid control system can function through a closed loop monitoring flow or volume/weight of fluid aspirated versus fluid irrigated or it can simply be set to a flow rate higher than the aspiration rate and allow the excess to drain away as is typical of arthroscopic procedures.

In summary, it can be seen from the foregoing that the embodiments of the present disclosure provide an ultrasonic horn assembly, a system, and a method of irrigating during ultrasonic surgical aspiration which overcomes known problems in the art of applying ultrasonic horns for fragmenting tissue in fluid filled cavities. More specifically, in the presently disclosed system, known problems associated with energy absorption or dispersion in ultrasonic tips by fluid along the tip length resulting from fluid filling the flue around the tip or being aspirated without air inside of the tip are minimized.

In a deep cavity, the utilization of a long or multi-wavelength tip is sufficient to isolate the irrigation fluid. In the present disclosure, the system provides isolation of the irrigation fluid in the ventricles of the brain, so as to be able to immerse the resonant tip into the cerebral fluid. The fluid regulation system of the present disclosure ensures that the irrigation rate matches or exceeds the aspiration rate so as to avoid draining the ventricle. This fluid control system can function through a closed loop monitoring flow or volume/weight of fluid aspirated versus fluid irrigated or it can simply be set to a flow rate higher than the aspiration rate and allow the excess to drain away as is typical of arthroscopic procedures.

An additional capability afforded by the ultrasonic horn assembly 100 is the capability of a user to see the tip of the horn during the surgical procedure. It is envisioned that the flue can be configured as part of an endoscope or can be configured with an optical fiber bundle included in the flue. With the availability of optical fiber bundles and micro lenses in the range of 0.5 to 1.0 mm in diameter, it is possible to insert the optic fiber bundle inside of the flue.

The ultrasonic horn assembly 100 of the present disclosure enables irrigating tissue such that irrigation fluid 186 is supplied only to a vibrating tip portion 166 of the ultrasonic horn 10, and an air path is provided so that the condition rendering the tip as inoperative is mitigated or completely eliminated, even in environments such as a ventricle of the brain, in which such conditions are most severe. Correspondingly, the system and method of the present disclosure enables supplying irrigating fluid only to the vibrating tip portion of the ultrasonic horn.

While the above description contains many specifics, these specifics should not be construed as limitations on the scope of the present disclosure, but merely as exemplifications of preferred embodiments thereof. Those skilled in the art will envision many other possible variations that are within the scope and spirit of the present disclosure.

What is claimed is:

1. An ultrasonic horn assembly comprising:
   a flue having a distal end;
   a housing disposed within the flue, the housing having a distal end;
   an elongated member operatively disposed within the housing, the elongated member having a distal end which has a vibrating tip portion protruding distally beyond the distal end of the housing and protruding distally beyond the distal end of the flue, the elongated member also having an internal channel extending through the elongated member including the vibrating tip portion, the channel being configured for aspiration;
   an optical viewing element operatively located within the flue and configured to view at least the vibrating tip portion;
   wherein the housing includes an inside surface that is larger than a diameter of the elongated member thereby creating a first internal space between the elongated member and the housing;
   wherein the flue has an inside surface that is larger than the housing thereby creating a second internal space separate from the first internal space and which is formed between the housing and the flue, the second internal space being open at the distal end of the flue, the flue being adapted such that irrigation fluid applied to the second internal space flows out the distal end of the flue over the vibrating tip portion of the elongated member; and
   a seal disposed between the housing and the elongated member at a position proximal to the vibrating tip portion, the seal configured to inhibit fluids entering into the first internal space from the distal end of the flue and to inhibit fluids exiting the first internal space at the distal end of the housing to reach the vibrating tip portion;
   wherein the internal channel of the elongated member includes an aperture located at a position on the elongated member that is proximal to the seal.

2. The ultrasonic horn assembly of claim 1, further comprising:
   an adapter having, a proximal end and a distal end, the proximal end of the adapter being configured to connect to an ultrasonic resonator;
   wherein the elongated member has a proximal end, the distal end of the adapter being joined to the proximal end of the elongated member; and
   wherein the internal channel of the elongated member is formed within the adapter and the elongated member, the internal channel being in fluidic communication with the aperture and the aperture configured to provide aspiration, the aperture being formed on an outer surface of the elongated member.

3. The ultrasonic horn assembly of claim 2, wherein the proximal end of the adapter includes a connecting portion for coupling with at least one of the elongated member and the ultrasonic resonator, and wherein the housing encloses the elongated member, the adapter, and the ultrasonic resonator.

4. The ultrasonic horn assembly of claim 1, further comprising:
   a supply of irrigation fluid fluidically coupled to the elongated member so as to supply irrigation fluid to the elongated member; and
   a source of suction aspiration fluidically coupled to the internal channel of the elongated member.

5. The ultrasonic horn assembly of claim 4, wherein the supply of irrigation fluid is fluidically coupled to the second internal space formed between the flue and the housing, and to a space between the flue and the distal end of the elongated member.

6. The ultrasonic horn assembly of claim 4, further comprising:
   a controller that controls the supply of irrigation fluid via monitoring of fluid level in a patient cavity during a surgical procedure; and
   a controller that controls the level of suction aspiration applied by the source of suction aspiration via monitoring of fluid level in the patient cavity during the surgical procedure.

7. The ultrasonic horn assembly of claim 6, wherein the controller that controls the supply of irrigation fluid via monitoring of fluid level in a patient cavity during a surgical procedure and the controller that controls the level of suction aspiration applied by the source of suction aspiration via monitoring of fluid level in the patient cavity during the surgical procedure are operatively coupled one to another to coordinate control of the fluid level in the patient cavity.

8. The ultrasonic horn assembly of claim 1, further comprising:
   a source of ultrasonic signal generating power operatively coupled to the elongated member; and circuitry controlling at least one of power, frequency and amplitude of the tip portion of the elongated member occurring as a result of operation of the source of ultrasonic signal generating power.

9. The ultrasonic horn assembly of claim 8, wherein the circuitry controlling at least one of power, frequency and amplitude of the tip portion of the elongated member occurring as a result of operation of the source of ultrasonic signal generating power controls at least one of the supply of irrigation fluid and the suction aspiration so as to minimize damping of vibration of the tip portion.

10. The ultrasonic horn assembly of claim 1, wherein the optical viewing element is disposed to enable viewing the vibrating tip portion of the ultrasonic horn.

11. The ultrasonic horn assembly of claim 10, wherein the optical viewing element is disposed within a channel member formed in the flue and extends to a distal end portion of the flue such that the optical viewing element is capable of viewing, through a viewing angle, the tip portion.

12. The ultrasonic horn assembly of claim 1, further comprising a controller for varying a position of the optical viewing element.

13. An ultrasonic horn assembly comprising:
a flue;
an adapter having a proximal end and a distal end, the proximal end of the adapter being configured to connect to an ultrasonic resonator;
an ultrasonic horn operatively disposed within the flue, the ultrasonic horn being configured to supply irrigating fluid only to a vibrating tip portion of the ultrasonic horn and to aspirate through a portion of the ultrasonic horn located proximally of the vibrating tip portion;
an elongated member having an outer surface, a proximal end and a distal end, the distal end of the adapter being joined to the proximal end of the elongated member;
an internal channel formed within the adapter and the elongated member, the internal channel extending from the proximal end of the elongated member to the distal end of the elongated member, the internal channel having a first aperture at a distal end thereof, the distal end of the elongated member being the vibrating tip portion of the ultrasonic horn, the elongated member having a second aperture formed in the outer surface thereof and being in fluidic communication with the internal channel;
an optical viewing element operatively connected to the flue and configured to view at least the vibrating tip portion of the ultrasonic horn; and
a housing having an inside surface and an outside surface, the inside surface of the housing at least partially encasing the elongated member, wherein a first internal space is defined between the housing and the elongated member;
wherein the flue at least partially encases the housing, the flue having an inside surface and an outside surface, the inside surface of the flue at least partially encasing the distal end of the elongated member, a second internal space is defined between the flue and the housing and between the flue and the distal end of the elongated member, the first internal space fluidically communicating with the second internal space via a passage formed in the housing, and the first internal space fluidically communicating with the internal channel formed within the elongated member via the second aperture formed in the elongated member.

14. The ultrasonic horn assembly of claim 13, further comprising a seal for inhibiting fluidic communication between the first internal space and the second internal space.

15. The ultrasonic horn assembly of claim 14, further comprising:
a supply of irrigation fluid fluidically coupled to the ultrasonic horn so as to supply irrigation fluid only to the vibrating tip portion of the ultrasonic horn; and
a source of suction aspiration fluidically coupled to the internal channel of the ultrasonic horn, only at a location proximal of the vibrating tip portion.

16. The ultrasonic horn assembly of claim 15, wherein
the supply of irrigation fluid is fluidically coupled to the second internal space formed between the flue and the housing, and to a space between the flue and the distal end portion of the elongated member; and
the source of suction aspiration is fluidically coupled to the internal channel formed within the adapter and the elongated member of the ultrasonic horn.

17. The ultrasonic horn assembly of claim 16, further comprising:
a controller that controls the supply of irrigation fluid via monitoring of fluid level in a patient cavity during a surgical procedure; and
a controller that controls the suction aspiration applied by the source of suction aspiration via monitoring of fluid level in the patient cavity during the surgical procedure.

18. The ultrasonic horn assembly of claim 17, wherein the controller that controls the supply of irrigation fluid via monitoring of fluid level in a patient cavity during a surgical procedure and the controller that controls the suction aspiration applied by the source of suction aspiration via monitoring of fluid level in the patient cavity during the surgical procedure are operatively coupled one to another to coordinate control of the fluid level in the patient cavity.

19. The ultrasonic horn assembly of claim 15, further comprising:
a source of ultrasonic signal generating power operatively coupled to the elongated member; and
circuitry controlling the source of ultrasonic signal generating power to thereby control at least one of power, frequency and amplitude of the vibrating tip portion of the ultrasonic horn as a result of operation of the source of ultrasonic signal generating power.

20. The ultrasonic horn assembly of claim 19, wherein the circuitry controlling the source of ultrasonic signal generating power to thereby control at least one of power, frequency and amplitude of the tip portion of the ultrasonic horn occurring as a result of operation of the source of ultrasonic signal generating power controls at least one of the supply of irrigation fluid and the suction aspiration so as to minimize damping of vibration of the tip portion of the ultrasonic horn.

21. The ultrasonic horn assembly of claim 13, wherein the proximal end of the adapter includes a connecting portion for coupling with at least one of the ultrasonic horn and an ultrasonic resonator, and wherein the housing encloses the elongated member, the adapter, and the ultrasonic resonator.

22. The ultrasonic horn assembly of claim 13, further comprising:
a supply of irrigation fluid fluidically coupled to the ultrasonic horn so as to supply irrigation fluid only to the vibrating tip portion of the ultrasonic horn; and
a source of suction aspiration fluidically coupled to the internal channel, only at a location proximal of the vibrating tip portion.

23. The ultrasonic horn assembly of claim 22, further comprising:
a source of ultrasonic signal generating power operatively coupled to the elongated member; and circuitry controlling the source of ultrasonic signal generating power to thereby control at least one of power, frequency and amplitude of the vibrating tip portion of the ultrasonic horn as a result of operation of the source of ultrasonic signal generating power.

24. The ultrasonic horn assembly of claim 13, wherein the optical viewing element is disposed to enable viewing the vibrating tip portion of the ultrasonic horn.

25. The ultrasonic horn assembly of claim 24, wherein the optical viewing element is disposed within a channel member formed in the flue and extends to a distal end portion of the flue such that the optical viewing element is capable of viewing, through a viewing angle, the tip portion of the ultrasonic horn.

26. The ultrasonic horn assembly of claim 24, further comprising a controller for varying a position of the optical viewing element.

* * * * *

UNITED STATES PATENT AND TRADEMARK OFFICE
CERTIFICATE OF CORRECTION

PATENT NO. : 7,871,392 B2
APPLICATION NO. : 11/330626
DATED : January 18, 2011
INVENTOR(S) : Joe D. Sartor It is certified that error appears in the above-identified patent and that said Letters Patent is hereby corrected as shown below:

Column 4, line 55, delete "102C2" and is larger than the diameter of the elongated member 102" and insert instead --102 and is larger than the diameter of the elongated member 102--.

Column 4, line 64 , between "larger than the" and ", so" delete "diameter of the elongated member 102" and insert instead --housing 104--.

Column 5, line 60, between "116" and "and second" delete "space 126".

Signed and Sealed this
Sixth Day of March, 2012

David J. Kappos
*Director of the United States Patent and Trademark Office*